United States Patent [19]

Hamazaki et al.

[11] 4,278,678
[45] Jul. 14, 1981

[54] SUBSTITUTED OXY-CYCLOHEXYLACETIC ACID DERIVATIVES

[75] Inventors: Yasuhiko Hamazaki; Kenji Seri; Nobuo Ishiyama; Toshiyuki Yamamoto; Masao Sakasai; Reiko Sato, all of Tokyo, Japan

[73] Assignee: Kaken Chemical Co., Ltd., Tokyo, Japan

[21] Appl. No.: 94,950

[22] Filed: Nov. 16, 1979

[30] Foreign Application Priority Data

Dec. 1, 1978 [JP] Japan ............... 53-147746

[51] Int. Cl.$^3$ ............ A61K 31/44; C07D 213/65; A61K 31/19
[52] U.S. Cl. ............ 424/263; 424/308; 424/317; 546/301; 560/53; 560/56; 560/59; 560/61; 560/62; 562/464; 562/466; 562/469; 562/471; 562/472
[58] Field of Search ............ 546/301; 560/53, 56, 560/59, 61, 62; 562/464, 466, 469, 471, 472; 424/263, 308, 317

[56] References Cited

U.S. PATENT DOCUMENTS

| | | | |
|---|---|---|---|
| 3,740,437 | 6/1973 | Harrison et al. | 562/466 |
| 3,755,603 | 8/1973 | Harrison et al. | 560/59 |
| 4,153,803 | 5/1979 | Thiele et al. | 560/61 |

FOREIGN PATENT DOCUMENTS

1598081  6/1970  France .................. 546/301

*Primary Examiner*—Henry R. Jiles
*Attorney, Agent, or Firm*—Oblon, Fisher, Spivak, McClelland & Maier

[57] ABSTRACT

Novel substituted oxy-cyclohexylacetic acid derivatives as antihyperlipidemic agents are given. The compounds have the formula

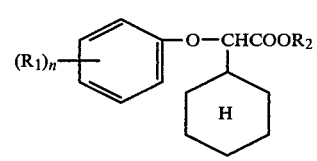

(I)

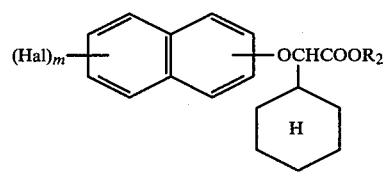

(II)

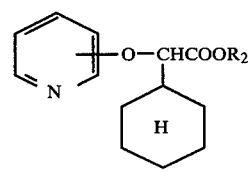

(III)

wherein n is 1 or 2; m is 0, 1 or 2; $R_1$ represents a halogen atom, trifluoromethyl, a lower alkyl, a lower alkoxy, a lower alkylcarbonyl, dimethylphenylmethyl, cyclohexyl, phenyl, halogenophenyl, phenoxy or halogenophenoxy group, and two of $R_1$ groups can be bonded to form an orthocondensed saturated alkylene ring; Hal represents a halogen atom; and $R_2$ represents a hydrogen atom or a lower alkyl group.

7 Claims, No Drawings

SUBSTITUTED OXY-CYCLOHEXYLACETIC ACID DERIVATIVES

BACKGROUND OF THE INVENTION

1. Field of the Invention

The present invention relates to novel substituted oxycyclohexylacetic derivatives, to preparations of such compounds and to antihyperlipidemic agents comprising such compounds as the active ingredients.

2. Description of the Prior Arts

It has been known to clinically use ethyl-α-(p-chlorophenoxy)isobutylate and analogous compounds; nicotinic acid derivatives; hormones such as protein assimilation steroids; unsaturated aliphatic acid such as linoleic acid; cholestyramine and β-sitosterols as antihyperlipidemic agents.

The inventors have studied and proposed various oxyacetic acid derivatives and their effects to human-bodies and have found that certain benzoyl phenoxy acetic acid derivatives have desired antihyperlipidemic properties.

The inventors have further found that superior compounds can be obtained by modifying them.

SUMMARY OF THE INVENTION

It is an object of the present invention to provide novel substituted oxy-cyclohexylacetic acid derivatives which are effective for remedy of hyperlipidemia.

It is the other object of the present invention to provide a process for producing novel substituted oxy-cyclohexylacetic acid derivatives.

The foregoing and other objects of the present invention have been attained by providing substituted oxy-cyclohexylacetic acid derivatives having the formula

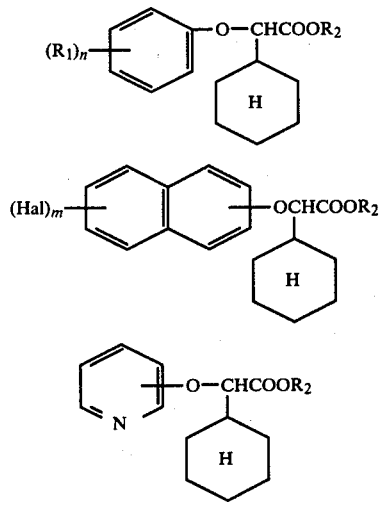

wherein n is 1 or 2; m is 0, 1 or 2; $R_1$ represents a halogen atom, trifluoromethyl, a lower alkyl, a lower alkoxy, a lower alkylcarbonyl, dimethylphenylmethyl, cyclohexyl, phenyl, halogenophenyl, phenoxy or halogenophenoxy group, and two of $R_1$ groups can be bonded to form an orthocondensed saturated alkylene ring; Hal represents a halogen atom; and $R_2$ represents a hydrogen atom or a lower alkyl group, which have excellent antihyperlipidemic activity.

DETAILED DESCRIPTION OF THE PREFERRED EMBODIMENTS

The inventors have studied preparations of various cyclohexylacetic acid derivatives and pharmacological characteristics of the cyclohexyl acetic acid derivatives.

As a result, it has been found that the novel substituted oxycyclohexylacetic acid derivatives having the formula (I), (II) or (III) have excellent antihyperlipidemic activity.

In the formula (I), a lower alkyl, a lower alkoxyl and a lower alkylcarbonyl group as the substituents means the substituents having a $C_1$-$C_4$ alkyl group which can be straight or branched chain form and a halogen atom can be —F, —Cl, —Br or —I.

The substituted phenyl group has one or two of substituents $R_1$ which can be the same or different and can form a saturated alkylene chain by an orthocondensation of two of $R_1$ whereby tetrahydronaphthyl group etc. can be formed as the substituted phenyl group.

In the formula (II), the naphthyl group which can be substituted by halogen atoms includes 1- or 2-naphthyl group and halogeno-1 or 2-naphthyl group.

In the formula (III), the pyridyl group includes 1-, 2-, or 3-pyridyl group.

The substituted cyclohexyl acetic acid derivatives (I), (II) or (III) can be produced by reacting a hydroxyl compound having the formula

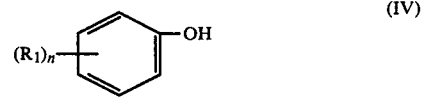

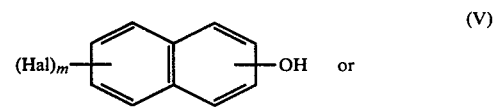

with an α-halogeno-cyclohexylacetic acid ester having the formula (VII)

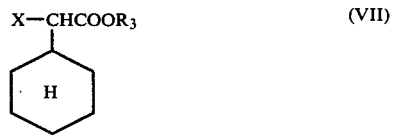

wherein X represents a halogen atom; and $R_3$ represents a lower alkyl group, and if necessary hydrolyzing the product.

In the production of the substituted oxy-cyclohexylacetic acid derivative (I), it is preferable to react the compound (IV), (V) or (VI) with the α-halogeno-cyclohexylacetate (VII) in the presence of a solvent.

The compounds having the formula (VII) wherein X is —I, —Br, or —Cl are preferably used. In the reaction, an equimolar amount of α-halogeno-cyclohexylacetate (VII) is usually reacted with the compound (IV), (V), or (VII). However, it is possible to use an excess of either the compound (VII) or the compound (IV), (V), or (VI).

The solvents are organic solvents inert under the reaction conditions such as dimethyl formamide and acetone. A mixed solvent can be used for the reaction.

For example, the reaction can be accelerated by adding a base such as potassium carbonate, sodium carbonate, sodium methylate or sodium ethylate.

It is possible to separate the reaction product obtained by reacting the base with the compound (IV), (V), or (VI) from the reaction system and then, to react the compound (VII) with the separated reaction product.

The reaction conditions such as temperature, time and pressure can be decided depending upon the starting materials, the solvent and the base.

The reaction is usually completed, at room temperaure, in 1 to 2 days or at 100° to 180° C. in 1 to 10 hours.

The corresponding carboxylic acids can be obtained by hydrolyzing the substituted oxy-cyclohexylacetic acid ester (I), (II), or (III). The hydrolysis can be carried out by the conventional processes. It is preferable to carry out the hydrolysis in an alkaline condition with an aqueous solution of sodium hydroxide or potassium hydroxide with an alcohol corresponding to $R_2$.

The reaction products (I), (II), or (III) can be separated and purified by conventional separating methods such as concentration, particularly concentration under reduced pressure; distillation; particularly distillation under a reduced pressure; fractional distillation; the adjustment of alkalinity or acidity; solvent extraction; crystallization; recrystallization; inversion and chromatography.

The novel substituted oxy-cyclohexylacetic acid derivatives (I), (II), or (III) have excellent antihyperlipidemic activity and are effective in practice as an antihyperlipidemic agent for hyperlipidemia remedy.

The substituted oxy-cyclohexylacetic acid derivatives (I), (II), or (III) have low toxicity and they do not cause hepatic disease (hepatitis) which is found by the administration of ethyl-α-(p-chlorophenoxy)-isobutyrate.

The antihyperlipidemic agents of the present invention comprising the substituted oxy-cyclohexylacetic acid derivatives (I), (II), or (III) can be orally administered in the form of tablets, capsules, powder or granules; and they can also be parenterally administered in the form of injectable solutions, suppositories or pellets.

The substituted oxy-cyclohexylacetic acid derivative (I), (II), or (III) can be combined with other antihyperlipidemic agents, a hypotensive agent or an anticoagulant agent.

The dose of the substituted oxy-cyclohexylacetic acid derivative (I), (II), or (III) is usually in a range of 25 to 2500 mg, preferably 200 to 1000 mg per day adult in oral dose.

The substituted oxy-cyclohexylacetic acid derivatives (I), (II), or (III) also have anticoagulant and antiinflammatory activities.

The invention will be further illustrated by the following examples.

EXAMPLE 1

Ethyl α-(p-ethylphenoxy)α-cyclohexylacetate

Into 30 ml of anhydrous ethanol, 575 mg (0.025 mole) of metallic sodium was dissolved and then, 3.05 g (0.025 mole) of p-ethylphenol was added. The mixture was stirred at room temperature for about 30 minutes. Ethanol was distilled off under a reduced pressure and 10 ml of dimethyl formamide was added to the residue and dimethyl formamide was distilled off under a reduced pressure and then, 30 ml of dimethyl formamide was added to the residue to dissolve it.

Into the solution, 5.0 g (0.02 mole) of ethyl α-bromo-α-cyclohexylacetate was added. The mixture was refluxed for 6 hours and then dimethyl formamide was distilled off under a reduced pressure. The residue was admixed with 50 ml of water and extracted twice with 100 ml of benzene. The benzene layers were combined and washed three times with 30 ml of 5% NaOH aq.sol. and then with water and dehydrated over sodium sulfate and distilled in vacuum to obtain 3.1 g of ethyl α-(p-ethylphenoxy)α-cyclohexylacetate (yield: 50%).

EXAMPLE 2

Ethyl α-(p-cyclohexylphenoxy)α-cyclohexylacetate

Into 30 ml of anhydrous ethanol, 575 mg (0.025 mole) of metallic sodium was dissolved and 4.4 g (0.025 mole) of p-cyclohexylphenol was added. The mixture was stirred at room temperature for about 30 minutes. Ethanol was distilled off under a reduced pressure and 10 ml of dimethyl formamide was added to the residue and dimethyl formamide was distilled off under a reduced pressure and then, 30 ml of dimethyl formamide was added to the residue to dissolve it.

Into the solution, 5.0 g (0.02 mole) of ethyl α-bromo-α-cyclohexylacetate was added. The mixture was refluxed for 8 hours and then dimethyl formamide was distilled off under a reduced pressure. The residue was admixed with 50 ml of water and extracted twice with 100 ml of benzene. The benzene layers were combined and washed three times with 30 ml of 5% NaOH aq.sol. and then with water and dehydrated over sodium sulfate and distilled in vacuum to obtain 3.8 g of ethyl α-(p-cyclohexylphenoxy)α-cyclohexylacetate (yield: 57.4%).

EXAMPLE 3

Ethyl α-(p-phenylphenoxy)α-cyclohexylacetate

Into 30 ml of anhydrous ethanol, 575 mg (0.025 mole) of metallic sodium was dissolved and 4.25 g (0.025 mole) of p-phenylphenol was added. The mixture was stirred at room temperature for about 30 minutes. Ethanol was distilled off under a reduced pressure and 10 ml of dimethyl formamide was added to the residue and dimethyl formamide was distilled off under a reduced pressure and then, 30 ml of dimethyl formamide was added to the residue to dissolve it.

Into the solution, 5.0 g (0.02 mole) of ethyl α-bromo-α-cyclohexylacetate was added. The mixture was refluxed for 7 hours and then dimethyl formamide was distilled off under a reduced pressure. The residue was admixed with 50 ml of water and extracted twice with 100 ml of benzene. The benzene layers were combined and washed three times with 30 ml of 5% NaOH aq.sol. and then with water and dehydrated over sodium sulfate and distilled in vacuum to obtain 2.55 g of ethyl α-(p-phenylphenoxy)α-cyclohexylacetate (yield: 37.7%).

EXAMPLE 4

Ethyl α-(5,6,7,8-tetrahydro-2-naphthoxy)-α-cyclohexylacetate

Into 30 ml of anhydrous ethanol, 575 mg (0.025 mole) of metallic sodium was dissolved and 3.7 g (0.025 mole) of 5,6,7,8-tetrahydro-2-naphthol was added. The mixture was stirred at room temperature for about 30 minutes. Ethanol was distilled off under a reduced pressure and 10 ml of dimethyl formamide was added to the residue and dimethyl formamide was distilled off under a reduced pressure and then, 30 ml of dimethyl formamide was added to the residue to dissolve it.

Into the solution, 5.0 g (0.02 mole) of ethyl α-bromo-α-cyclohexylacetate was added. The mixture was refluxed for 6 hours and then dimethyl formamide was distilled off under a reduced pressure. The residue was admixed with 50 ml of water and extracted twice with 100 ml of benzene. The benzene layers were combined and washed three times with 30 ml of 5% NaOH aq.sol. and then with water and dehydrated over sodium sulfate and distilled in vacuum to obtain 3.2 g of ethyl α-(5,6,7,8-tetrahydro-2-naphthoxy)-α-cyclohexylacetate (yield: 50.7%).

EXAMPLE 5

Into 15 ml of anhydrous ethanol, 205 mg (0.0089 mole) of metallic sodium was dissolved and then, 1.8 g (0.0089 mole) of p-phenoxyphenol was added. The mixture was stirred at room temperature for about 30 minutes. Ethanol was distilled off under a reduced pressure and 5 ml of dimethyl formamide was added to the residue and dimethyl formamide was distilled off under a reduced pressure and then, 15 ml of dimethyl formamide was added to the residue to dissolve it. Into the solution, 2.5 g (0.010 mole) of ethyl α-bromo-α-cyclohexylacetate was added. The mixture was refluxed for 8 hours and then diemethyl formamide was distilled off under a reduced pressure. The residue was admixed with 50 ml of water and extracted twice with 50 ml of benzene. The benzene layers were combined and washed three times with 30 ml of 5% NaOH aq.sol. and then with water and dehydrated over sodium sulfate and distilled in vacuum to obtain 1.4 g of ethyl α-(p-phenoxyphenoxy)α-cyclohexylacetate (yield: 42.6%).

EXAMPLE 6

Into 15 ml of ethanol, 430 mg of potassium hydroxide was dissolved and 1.7 g (0.00512 mole) of ethyl α-(p-cyclohexylphenoxy)α-cyclohexylacetate was added. The mixture was heated on a water bath at 65° to 70° C. for 90 minutes and then ethanol was distilled off under a reduced pressure and the residue was admixed with water and washed twice with benzene. The water layer was acidified with 10% HCl aq.sol. to precipitate a precipitate. The precipitate was filtrated and washed with water and dried. The product was recrystallized from n-hexane to obtain 0.7 g of α-(p-cyclohexylphenoxy)α-cyclohexylacetic acid (yield: 44.9%).

Physical properties of the compounds of Examples 1 to 6 and the other compounds produced by the similar process are shown in Table 1.

TABLE 1

$$R^3-O-CHCOOR^2$$
(with H on a cyclohexyl ring)

| Comp. No. | $R^3$ | $R^2$ | Boiling point (°C./mmHg) | IR direct ν C=O cm$^{-1}$ |
|---|---|---|---|---|
| 1 |  | $C_2H_5$ | 117–118/0.15 | 1755 |
| 2 |  | $C_2H_5$ | 133–135/0.275 | 1760 |
| 3 |  | $C_2H_5$ | 170–172/1 | 1755 |
| 4 |  | $C_2H_5$ | 145–148/1 | 1760 1745 |
| 5 |  | $C_2H_5$ | 167–169/0.32 | 1760 1740 |
| 6 (Exp. 3) |  | $C_2H_5$ | 194–198/0.055 | 1750 |
| 7 (Exp. 2) |  | $C_2H_5$ | 148–150/0.325 | 1765 1745 |
| 8 |  | $C_2H_5$ | 165–167/0.175 | 1765 1745 |
| 9 |  | $C_2H_5$ | 210–212/0.1 | 1765 1745 |
| 10 (Exp. 4) |  | $C_2H_5$ | 170–173/0.1 | 1762 1743 |
| 11 |  | $C_2H_5$ | 170–173/0.125 | 1760 1750 1690 (>C=O) |
| 12 |  | $C_2H_5$ | 180–182/0.12 | 1755 1700 (>C=O) |
| 13 |  | $C_2H_5$ | 128–130/0.1 | 1760 1745 |
| 14 Exp. 1) |  | $C_2H_5$ | 135–137/0.24 | 1760 1742 |
| 15 |  | $C_2H_5$ | 178–181/0.15 | 1745 |
| 16 (Exp. 5) |  | $C_2H_5$ | 192–195/0.12 | |
| 17 |  | $C_2H_5$ | 205–208/0.03 | |
| 18 |  | $C_2H_5$ | 185–189/0.045 | |

TABLE 1-continued $$R^3-O-CHCOOR^2$$

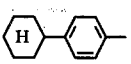

| Comp. No. | $R^3$ | $R^2$ | Boiling point (°C./mmHg) | IR direct $\nu$ C=O cm$^{-1}$ |
|---|---|---|---|---|
| 19 (Exp. 6) | H—⟨ ⟩—⟨ ⟩— | H | Melting point 99–100° C. | |

| Compound No. | NMR (CDCl$_3$) $\delta$ (ppm) |
|---|---|
| 1 | 1.21(t, 3H), 1.04–2.22(m, 11H), 4.18(q, 2H), 4.37(d, 1H), 7.18–7.30(m, 2H), 6.98–7.12(m, 2H) |
| 2 | 1.21(t, 3H), 0.93–2.33(m, 11H), 4.41(d, 1H), 7.10–7.23(m. 2H), 8.13–8.33(m, 2H) |
| 3 | 1.20(t, 3H), 0.90–2.24(m, 11H), 4.16(q, 2H), 4.30(d, 1H), 6.76(d, 2H), 7.14(d, 2H) |
| 4 | 1.11(t, 3H), 0.95–2.18(m, 11H), 2.28(s, 6H), 4.04(q, 2H), 4.37(d, 1H), 6.85–7.19(m, 3H) |
| 5 | 1.18(t, 3H), 0.92–2.16(m, 11H), 3.64(s, 3H), 4.12(q, 2H), 4.21(d, 1H), 6.72(s, 4H) |
| 6 (Example 3) | 1.14(t, 3H), 0.67–2.18(m, 11H), 4.10(q, 2H), 4.29(d, 1H), 6.82(d, 2H), 7.22(d, 2H), 7.2–7.5(m, 5H) |
| 7 (Example 2) | 1.23(t, 3H), 0.84–2.24(m, 22H), 4.18(q, 2H), 4.29(d, 1H), 6.76(d, 2H), 7.05(d, 2H) |
| 8 | 0.79(t, 3H), 1.22(t, 3H), 1.18(d, 3H), 1.32–1.61(m, 2H), 0.95–2.24(m, 11H), 2.41–2.55(m, 1H), 4.18(q, 2H), 4.31(d, 1H), 6.76(d, 2H), 7.02(d, 2H) |
| 9 | 1.23(t, 3H), 1.63(s, 6H), 0.78–2.13(m, 11H), 4.18(q, 2H), 4.23(d, 2H), 6.73(d, 2H), 7.07(d, 2H), 7.18(m, 5H) |
| 10 (Example 4) | 1.23(t, 3H), 1.72(m, 4H), 0.78–2.18(m, 11H), 2.65(m, 4H), 4.17(q, 2H), 4.28(d, 1H), 6.62(s, 1H), 6.59(d, 1H), 6.88(d, 1H) |
| 11 | 1.23(t, 3H), 0.90–2.24(m, 11H), 2.51(s, 3H), 4.26(q, 2H), 4.46(d, 1H), 6.87(d, 2H), 7.87(d, 2H) |
| 12 | 1.24(t, 3H), 0.84–2.24(m, 11H), 2.54(s, 3H), 4.19(q, 2H), 4.44(d, 1H), 6.76–7.55(m, 4H) |
| 13 | 1.23(t, 3H), 0.78–2.13(m, 11H), 2.28(s, 3H), 4.18(q, 2H), 4.33(d, 1H), 6.68(s, 3H), 7.09(t, 1H) |
| 14 (Example 1) | 1.23(t, 3H), 1.18(t, 3H), 0.84–2.18(m, 11H), 2.56(q, 2H), 4.18(q, 2H), 4.23(d, 1H), 6.76(d, 2H), 7.04(d, 2H) |
| 15 | 1.20(t, 3H), 084–2.35(m, 11H), 4.17(q, 2H), 4.54(d, 1H), 6.55(d, 1H), 7.35(d, 1H), 7.54(t, 2H), 8.16–8.36(m, 2H) |
| 16 (Example 5) | 1.29(t, 3H), 0.88–2.13(m, 11H), 4.09(q, 2H), 4.20(d, 1H), 6.44–7.28(m, 9H) |
| 17 | 1.26(t, 3H), 0.95–2.24(m, 11H), 4.26(q, 2H), 4.30(d, 1H), 6.80(d, 2H), 6.83(s, 4H), 7.21(d, 2H) |
| 18 | 1.24(t, 3H), 0.86–2.24(m, 11H), 4.20(q, 2H), 4.28(d, 1H), 6.82(d, 2H), 6.86(s, 4H), 7.19(d, 2H) |
| 19 (Example 6) | 0.86–2.14(m, 22H), 4.36(d, 2H), 6.82(d, 2H), 7.06(d, 2H) |

Preparation 1

A 400 g of ethyl α-(p-phenylphenoxy)-α-cyclohexylacetate, 400 g of fine powdery silicone and 185 g of corn starch were uniformly mixed and charged in a kneader and 1000 ml of 3% aqueous solution of hydroxypropyl cellulose was added and the mixture was kneaded. The mixture was granulated by passing it through the 16 mesh screen to form uniform granules which comprises an antihyperlipidemic agent.

Preparation 2

A 400 g of ethyl α-(p-phenylphenoxy)-α-cyclohexylacetate, 400 g of lactose and 175 g of potato starch were uniformly mixed and charged in a kneader and 3% aqueous solution of hydroxypropyl cellulose was added and the mixture was kneaded and granulated by passing through a 16 mesh screen and 0.3% of magnesium stearate was added and the mixture was compressed to form tablets which comprise an antihyperlipidemic agent.

Test 1

The antihyperlipidemic activity in rats with dietary hyperlipidemia.

In the tests, Wister type male rats (weight: 140 g) were used in groups of 6 each.

A feed containing 2% of cholesterol, 1% of sodium cholate and 5% of coconut oil was given for 4 days to cause hyperlipidemia.

Each active ingredient was suspended in a 1% aqueous solution of Tween 80 (® polyoxyethylene sorbitane monoalkylate) and the suspension was orally administered in a dose of 100 mg/kg once daily for 4 days starting with the supply of the cholesterol supplemented diet.

After 24 hours from the administration, blood was sampled and the concentration of total cholesterols in blood-plasma was measured by the method described in Clinical chemistry Vol. 22 page 393 (1968) and the concentration of triglyceride (neutral fat) was measured by Fletcher method (Clinica Chimica Acta) Vol. 10 page 451 (1964).

The results are shown in Table 2.

As the active ingredients, the compounds of the invention shown in Table and ethyl-α-(p-chlorophenoxy)-isobutylate having the formula

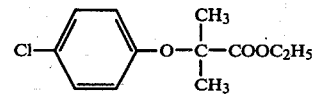

were used.

Test 2

In the acute toxicity tests, male mice (weight: 22 to 25 g) were used in groups of 10 each.

Each active ingredient was dissolved in olive oil and the solution was orally administrated in a volume corresponding to the body weight.

LD$_{50}$ was calculated by the area method from the mortal percent after 72 hours from the administration.

The results are also shown in Table 2.

TABLE 2

| Compound No. | Antihypertipidemic activity (%) Cholesterol | Triglyceride | Acute toxicity LD$_{50}$ (mg/kg) |
|---|---|---|---|
| 1 | 12.1 | 49.3 | 2500 |
| 2 | 0 | 45.0 | 2500 |
| 3 | 43.3 | 31.5 | >3000 |
| 4 | 38.5 | 0 | >3000 |
| 5 | 39.0 | 8.9 | >3000 |
| 6 | 52.3 | 44.0 | >3000 |
| 7 | 42.6 | 51.6 | >3000 |
| 8 | 36.7 | 17.1 | >3000 |
| 9 | 40.3 | 28.1 | >3000 |
| 10 | 52.1 | 44.4 | 2500 |
| 11 | 31.8 | 30.9 | >3000 |
| 12 | 14.3 | 11.5 | >3000 |
| 13 | 7.9 | 59.7 | >3000 |
| 14 | 42.6 | 64.8 | >3000 |
| 15 | 0 | 53.0 | 2500 |
| 16 | 40.8 | 38.7 | >3000 |

TABLE 2-continued

| Compound No. | Antihypertipidemic activity (%) Cholesterol | Triglyceride | Acute toxicity $LD_{50}$ (mg/kg) |
| --- | --- | --- | --- |
| 17 | 45.3 | 46.5 | >3000 |
| 18 | 43.7 | 40.5 | >3000 |
| 19 | 35.8 | 32.4 | >3000 |

What is claimed is:

1. A substituted oxy-cyclohexylacetic acid derivative having the formula

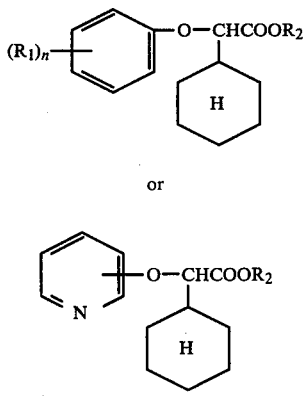

wherein n is 1 or 2; $R_1$ represents a halogen atom, trifluoromethyl, a lower alkyl, a lower alkoxy, a lower alkylcarbonyl, dimethylphenylmethyl, cyclohexyl, phenoxy or halogenophenoxy group, and two of $R_1$ groups can be bonded to form an orthocondensed saturated alkylene ring; and $R_2$ represents a hydrogen atom or a lower alkyl group.

2. A substituted oxy-cyclohexylacetic acid derivative having the formula (I) according to claim 1 wherein $R_1$ represents a halogen atom, a lower alkyl, cyclohexyl, phenoxy or halogenophenoxy group.

3. A substituted oxy-cyclohexylacetic acid derivative having the formula (I) according to claim 1 wherein two of $R_1$ groups form an orthocondensed saturated alkylene ring.

4. A derivative according to claim 1 comprising a lower alkylphenoxy cyclohexylacetic acid or a lower alkyl ester thereof.

5. A derivative according to claim 1 comprising a cyclohexylphenoxy cyclohexylacetic acid or a lower alkyl ester thereof.

6. A derivative according to claim 1 comprising a pyridyloxy cyclohexylacetic acid or a lower alkyl ester thereof.

7. An antihyperlipidemic composition which comprises as an active ingredient, an antihyperlipidemically effective amount of a substituted oxy-cyclohexylacetic acid derivative having the formula (I) or (III) according to claim 1, in a pharmaceutically acceptable carrier.

* * * * *